(12) United States Patent
Harris et al.

(10) Patent No.: US 8,261,739 B2
(45) Date of Patent: Sep. 11, 2012

(54) DRY POWDER INHALERS

(75) Inventors: David Stuart Harris, Milton (GB); Simon James Smith, Hertford (GB)

(73) Assignee: Cambridge Consultants Limited (GB)

( * ) Notice: Subject to any disclaimer, the term of this patent is extended or adjusted under 35 U.S.C. 154(b) by 1164 days.

(21) Appl. No.: 11/658,693

(22) PCT Filed: Dec. 9, 2005

(86) PCT No.: PCT/GB2005/004742
§ 371 (c)(1),
(2), (4) Date: Sep. 25, 2007

(87) PCT Pub. No.: WO2006/061637
PCT Pub. Date: Jun. 15, 2006

(65) Prior Publication Data
US 2008/0314384 A1      Dec. 25, 2008

(30) Foreign Application Priority Data

Dec. 9, 2004    (GB) .................................. 0427028.6

(51) Int. Cl.
*A61M 15/00* (2006.01)
*A61M 11/06* (2006.01)
(52) U.S. Cl. ......... 128/203.15; 128/203.12; 128/203.19; 128/203.21; 128/203.23; 128/205.25; 239/338; 239/370
(58) Field of Classification Search ............ 128/200.24, 128/203.12, 203.15, 203.19, 203.21, 203.23, 128/203.25; 239/338, 370
See application file for complete search history.

(56) References Cited

U.S. PATENT DOCUMENTS

| 3,362,405 | A | * | 1/1968 | Hazel ..................... 128/203.15 |
| 3,960,734 | A | * | 6/1976 | Zagorski ................... 210/512.2 |
| 4,155,359 | A | * | 5/1979 | Zagorski ................. 128/206.15 |
| 4,304,360 | A | * | 12/1981 | Luhr et al. ..................... 241/5 |
| 4,762,148 | A | * | 8/1988 | Marui et al. .................. 137/808 |
| 5,186,166 | A |   | 2/1993 | Riggs et al. |
| 5,207,217 | A |   | 5/1993 | Cocozza et al. |
| 5,337,740 | A |   | 8/1994 | Armstrong et al. |
| 5,355,872 | A |   | 10/1994 | Riggs et al. |
| 5,458,135 | A | * | 10/1995 | Patton et al. ............. 128/200.14 |
| 5,476,093 | A | * | 12/1995 | Lankinen ................. 128/203.15 |

(Continued)

FOREIGN PATENT DOCUMENTS

EP    1 208 863    5/2002

(Continued)

OTHER PUBLICATIONS

International Search Report; PCT/GB2005/004742; Jul. 4, 2006.

*Primary Examiner* — Clinton T Ostrup
(74) *Attorney, Agent, or Firm* — Cantor Colburn LLP

(57) ABSTRACT

A dry powder inhaler has a main airflow path including a cyclone chamber (16) having an air inlet and being so shaped that at least a part of the chamber decreases in cross-sectional area in a direction away from the air inlet, so as thereby in use to set up a reverse flow cyclone in the chamber. A bypass airflow path (8) bypasses the cyclone chamber and the main and bypass airflow paths communicate with a mouthpiece (6). The cyclone chamber may be provided by a part (22) which is removable from the rest of the inhaler for regular replacement thereof.

31 Claims, 13 Drawing Sheets

U.S. PATENT DOCUMENTS

| | | | |
|---|---|---|---|
| 5,529,059 A | 6/1996 | Armstrong et al. | |
| 5,596,982 A | 1/1997 | Blaha-Schnabel | |
| 5,715,810 A | 2/1998 | Armstrong et al. | |
| 6,209,538 B1 | 4/2001 | Casper et al. | |
| 6,270,545 B1 * | 8/2001 | Lee et al. | 55/345 |
| 6,273,086 B1 * | 8/2001 | Ohki et al. | 128/203.21 |
| 6,408,846 B1 | 6/2002 | Ohki et al. | |
| 6,550,477 B1 | 4/2003 | Casper et al. | |
| 6,575,160 B1 | 6/2003 | Volgyesi | |
| 6,595,210 B2 | 7/2003 | Ohki et al. | |
| 6,604,522 B2 | 8/2003 | Arvidsson et al. | |
| 6,606,992 B1 * | 8/2003 | Schuler et al. | 128/203.15 |
| 6,609,992 B2 * | 8/2003 | Kusumoto et al. | 475/318 |
| 6,637,431 B2 | 10/2003 | Ekelius et al. | |
| 6,655,381 B2 | 12/2003 | Keane et al. | |
| 6,668,827 B2 * | 12/2003 | Schuler et al. | 128/203.21 |
| 6,722,363 B1 | 4/2004 | Von Schuckmann | |
| 6,748,947 B2 | 6/2004 | Keane et al. | |
| 6,810,872 B1 | 11/2004 | Ohki et al. | |
| 6,819,872 B2 | 11/2004 | Farries et al. | |
| 6,871,646 B2 | 3/2005 | Keane et al. | |
| 6,932,082 B2 | 8/2005 | Stein | |
| 7,143,765 B2 | 12/2006 | Asking et al. | |
| 7,810,494 B2 * | 10/2010 | Harmer et al. | 128/203.21 |
| 2001/0029947 A1 * | 10/2001 | Paboojian et al. | 128/203.15 |
| 2002/0006316 A1 | 1/2002 | Schuler et al. | |
| 2002/0073997 A1 | 6/2002 | Keane et al. | |
| 2004/0107963 A1 | 6/2004 | Finlay et al. | |
| 2004/0159321 A1 * | 8/2004 | Eason et al. | 128/203.15 |
| 2004/0211419 A1 | 10/2004 | Eason et al. | |
| 2006/0147389 A1 | 7/2006 | Staniforth et al. | |
| 2009/0320837 A1 * | 12/2009 | Smith et al. | 128/203.15 |
| 2010/0212667 A1 * | 8/2010 | Smith et al. | 128/203.15 |

FOREIGN PATENT DOCUMENTS

| | | |
|---|---|---|
| EP | 1 330 280 | 7/2003 |
| EP | 1 475 115 | 11/2004 |
| FR | 2 352 556 | 5/1976 |
| GB | 2 340 758 | 3/2000 |
| GB | 2 420 982 | 6/2006 |
| WO | WO 99/13930 | 3/1999 |
| WO | WO 99/65550 | 12/1999 |
| WO | WO 01/00262 | 1/2001 |
| WO | WO 02/053216 | 7/2002 |
| WO | WO 03/089036 | 10/2003 |
| WO | WO 2004/103446 | 12/2004 |
| WO | WO 2005/025656 | 3/2005 |
| WO | WO 2005/037353 | 4/2005 |

* cited by examiner

| Configuration | A | B | C | D | E |
|---|---|---|---|---|---|
| Sketch | f10, 14 | 3.9, f14, 7, 20 | 4.7, f17, 8.6, 24.3 | 5.5, f20, 10, 28.6 | 3.9, f14, 7, 28 |
| Objective | Multi-dose | Small cut point | Medium cut point | Largest cut point | Elongated 2:1 aspect ratio |
| Diameter (mm) | 10 | 14 | 17 | 20 | 14 |
| Length (mm) | 14 | 20 | 24.3 | 28.6 | 28 |
| Cut-off dia (mm) | TBC | 3~4 | 4~5 | 5~6 | 3~4 |
| D P (Pa) | TBC | 61 | 25 | 12 | 21 |

| Device Type | Flow Rate (l min$^{-1}$) | % Active in Formulation | Fine Particle Fraction (%) | Mean Mass Aerodynamic Diameter (μm) |
|---|---|---|---|---|
| Conventional DPI 1 | 28.3 | 15 | 34.53 | 3.85 |
| Conventional DPI 2 | 28.3 | 15 | 37.31 | 3.79 |
| Cyclone E | 28.3 | 15 | 75.73 | 2.44 |
| Cyclone D | 28.3 | 15 | 79.10 | 2.56 |
| Cyclone C | 28.3 | 15 | 80.60 | 2.31 |
| Cyclone B | 28.3 | 15 | 78.65 | 2.39 |
| Cyclone A | 23.0 | 15 | 69.15 | 2.65 |

DRY POWDER INHALERS

TECHNICAL FIELD OF THE INVENTION

This invention relates to inhalers for delivering substances in powder form to the respiratory system of a user by inhalation.

DESCRIPTION OF THE RELATED ART

Dry Powder Inhalers (DPIs) are conventionally used to deliver active drug substances to the lungs of a user to treat asthma and other respiratory diseases. The basic principle upon which such inhalers work is that the user holds the inhaler to his or her mouth and draws breath through the device, thereby setting up a flow of air which entrains drug particles so that they are drawn into the user's respiratory system. The drug may be in the form of a free powder, or more commonly the drug is bound to carrier particles such as lactose. Of course, a blend of drug particles may be used.

The combined, aggregate particle size of the drug particle and carrier particle is generally greater than 1-5 μm (microns) which is the target size range for particles to be effectively inspired into the deep part of the lungs. DPIs therefore need to de-aggregate the particles (that is to separate the drug particles of respirable size from the larger carrier particles).

Furthermore, there is a tendency for the respirable particles to aggregate during storage. The DPI should there de-aggregate these fine (respirable) particles. Despite this, known DPIs are rather inefficient at de-aggregating the drug particles. The number of particles of respirable size as a proportion of the total output of the inhaler is known as the Fine Particle Fraction (FPF). In typical conventional inhalers, the Fine Particle Fraction can be as low as 30% and 40-50% is typical. Moreover, in many devices the FPF is dependent upon the inhalation flow rate of the user so that performance is inconsistent both between users and from one use to the next. Of course, a low FPF also leads to much of the drug being wasted. The additional problem with the FPF being inconsistent is that it is then impossible to control the dose actually being received by the user.

A low FPF is of particular concern since the particles which are not fully inhaled tend to hit the back of the user's throat and are deposited there. There is some evidence to suggest a link between deposition of steroid-based drugs on a user's throat and an increased risk of throat or lung cancer.

A further problem with existing dry powder inhalers is that the carrier particles (e.g. lactose) also tend to be inhaled and hit the back of the throat which gives rise to an unpleasant gritty feel. The build up of lactose also can be a contributing factor towards thrush.

Conventional DPIs are usually susceptible to moisture which can affect both the FPF and the delivered dose consistency.

There have been several proposals in the art for arrangements in which the Fine Particle Fraction is increased. However, these devices often have several other drawbacks. Firstly, they require active systems such as pressurized air which means that they are complex and therefore expensive to manufacture; and bulky and inconvenient to use. As they typically require significant manual force to be applied before inhalation, they take longer to use and cannot be used by those with impaired dexterity. Furthermore, such arrangements operate with single doses as opposed to metering a dose from a bulk storage. Finally, such arrangements tend to be operable only in a particular orientation.

BRIEF SUMMARY OF THE INVENTION

The invention provides a dry powder inhaler which alleviates at least some of the problems set out above.

When viewed from a first aspect the invention provides a dry powder inhaler comprising: a main airflow path including a cyclone chamber having an air inlet and being so shaped that at least a part of the chamber decreases in cross-sectional area in a direction away from the air inlet, so as thereby in use to set up a reverse flow cyclone in the chamber; and a bypass airflow path bypassing the cyclone chamber; wherein the main and bypass airflow paths communicate with a mouthpiece.

Thus it will be seen by those skilled in the art that in accordance with the invention the user's breath is drawn through two distinct paths—namely the main and bypass airflow paths—and that the main airflow path includes a reverse-cyclone chamber. The main path entrains the required powdered substance and passes it through the cyclone chamber in which a reverse-flow cyclone is set up. The reverse flow cyclone referred to herein has a particular meaning distinct from the general usage of the term cyclone in the art to mean any form of circulating air. A reverse-flow cyclone is one in which the air circulates in two generally concentric columns in opposite axial directions.

This arrangement is particularly advantageous in the present application for a number of reasons.

Firstly, the flow pattern in a reverse-flow cyclone—with an outer, downwardly spiralling "free" vortex and an inner, upwardly spiralling "forced" vortex—gives rise to a substantial fluctuation in tangential velocity across the width of the chamber. The steep velocity gradient encountered in the flow cause efficient de-aggregation of the particles. Moreover, the particles are subjected to these relatively high shear forces both as they travel downwardly to the base of the chamber and also as they travel back up the chamber in the inner, forced vortex. This relatively long flow path over substantially the whole of which de-aggregation can take place leads to a significantly increased proportion of fine particles within the entrained airflow as it travels towards the exit of the cyclone chamber.

Secondly, the central, forced vortex, which travels up from the base of the chamber is relatively tight and well defined. As is known in the art, the mean radius of circulation of a particle is dependent upon its weight and therefore size. Thus by careful selection of a particular circulation radius, a very sharp cut-off threshold of particle sizes may be achieved. By selecting a radius equivalent to 5 microns or less, an even higher Fine Particle Fraction may be achieved. Such selectivity can be obtained for example, by a "vortex finder" comprising a tube projecting some way into the cyclone chamber, which provides the outlet to the chamber.

Thirdly, the reversal of vertical direction of travel of the particles at the base of the chamber causes the de-aggregated carrier particles, and any drug or combination particles which are too large, to be trapped within the cyclone and thus not be inhaled by the user. This substantially reduces the deposition of large particles on the user's throat with the attendant problems referred to previously. The separation of the large particles retained in the inhaler from the finer particles which are inhaled is seen as an important benefit which may be achieved in accordance with the invention.

Fourthly, the residence time of the particles is greatly increased (therefore giving a greater number of opportunities for separation). Typically in a conventional DPI all drug is evacuated within 0.5 seconds. In accordance with preferred embodiments of the invention, particles remain within the device for the full duration of inhalation. This maximizes the shear forces for a given energy input. In accordance with the invention, only a proportion of the air inhaled by a user is drawn through the cyclone chamber. The remainder is drawn through the bypass airflow path into the mouthpiece without passing through the cyclone chamber. The Applicant has found that this bypass airflow is important in limiting the flow rate through the cyclone chamber, and controlling the overall device airflow resistance as felt by the user. If there is too great a flow rate through the cyclone chamber, then the velocity of the particles is too great and so even the fine respirable particles are separated and hence retained in the cyclone. Therefore the cyclone must be sufficiently large to allow the respirable particles to escape for a given flow rate. In practice this could mean that the chamber would be too large to be incorporated in an easily portable device such as can be carried in a pocket or handbag.

However by using the bypass, the flow rate through the chamber may be limited without having to increase the overall inhalation resistance of the inhaler, which would undesirably increase the time required for a user to draw a full breath through the device.

The relative resistances of the main and bypass airflow paths may be set during manufacture so as to give a predetermined flow rate through cyclone at a standard average inhalation flow rate. This may be found to give satisfactory results. However, if it is desired to enhance the consistency of Fine Particle Fraction and delivered dose it is preferred in accordance with at least some embodiments to provide means for varying the flow resistance of the bypass air flow path such that said resistance is decreased at increasing inhalation flow rates. In accordance with such a feature, the flow rate through the cyclone chamber may be kept more consistent even in the face of a varying rate of inhalation by the user since the resistance in the bypass path will automatically adjust with the user's rate of inhalation. For example, if the user inhales harder than average, the resistance in the bypass airflow path will decrease thereby allowing a greater bypass airflow to meet the excess flow rate without increasing the flow rate through the cyclone chamber to the same extent or, ideally, at all.

The above mentioned variable flow resistance in the bypass path could be achieved in a number of ways. In a simple example, one or more resiliently biased flaps could be provided extending across all or part of the bypass airflow path. In one convenient embodiment envisaged, a star-valve could be utilized. These generally comprise a plug of resilient material across a tube with a series of radial slits which allow individual segments to flex outwardly thereby allowing fluid to flow past the valve. The characteristics of such valves is that as the flow rate of fluid through them increases, the deflection of the individual segments also increases, thereby enlarging the generally star-shaped aperture which is created. Such a method is commonly to be found on domestic containers for viscous fluids such as sauces, toiletries etc.

In accordance with the invention the bypass air flow and the main airflow will meet, either before or upon reaching the mouthpiece. The way in which the airflows mix upon meeting is not critical to the basic operation of the invention. However, in some preferred embodiments the bypass airflow is arranged to surround the air which has passed through the cyclone chamber and which therefore has the substance particles entrained in it. The Applicant has appreciated that this is beneficial in helping to prevent the deposition of substance particles on the inner surface of the mouthpiece by reducing the residual angular velocity of particles exiting the cyclone chamber and by ensuring the particles which leave the circulating flow have a reduced chance of them being depositing on to the inside walls. By directing the bypass air along the walls of the mouthpiece of mixing chamber, this air will tend to flow along the wall from the Coanda effect.

The cyclone chamber could be provided as an integral part of the inhaler. However, the Applicant has appreciated that there is a minor potential drawback in this arrangement in that although the carrier particles are beneficially retained in the cyclone chamber rather than being inhaled by the user, the accumulation of carrier particles and large drug or combination particles, particularly at the base of the cyclone chamber is undesirable, not least because it could lead to them being re-entrained with subsequent doses. If an integral cyclone chamber is provided, this problem could be overcome by providing a door, flap, plug or the like which could be periodically removed to allow carrier particles to be emptied from the chamber. However, this is not ideal as such cleaning out is likely to be fiddly and messy and therefore unlikely to be carried out sufficiently regularly.

In accordance with a particularly preferred feature devised by the Applicant the cyclone chamber is provided by a detachable part. This could be embodied in a multi-part device which can be disassembled to facilitate cleaning/emptying of the sort referred to above, but much more advantageously it allows the cyclone chamber to be regularly replaced, preferably after every use—i.e. the cyclone chamber is provided by a disposable part.

This feature is novel and beneficial in its own right, not just in the context of the other features set forth above and thus when viewed from a second aspect the invention provides a dry powder inhaler comprising a chamber in which in use air and entrained substance particles can circulate and a mouthpiece in communication with said circulation chamber, wherein the circulation chamber is provided by a part which is removable from the rest of the inhaler for regular replacement thereof.

This aspect of the invention extends to the replaceable part per se and this when viewed from a further aspect the invention provides a removable part for a dry powder inhaler, said part comprising a chamber in which use air and entrained substance particles can circulate. It will be appreciated by those skilled in the art that by providing the circulation or cyclone chamber in a disposable part, the drawbacks referred to above associated with retained carrier particles are obviated since after every one or more uses, the parts including the chamber may be discarded and a fresh one installed. This also makes the device more hygienic generally.

Preferably, the circulation chamber is shaped such that at least a part of the chamber decreases in cross-sectional area in a direction away from the air inlet, so as thereby in use to set up a reverse flow cyclone in the chamber. Preferably, the inhaler comprises a bypass airflow path which bypasses the circulation chamber; Where a reverse-cyclone chamber as previously defined is provided, in accordance with either aspect of the invention, the decreasing cross-sectional area could be achieved in a number of ways. To give one example, the chamber could be generally cylindrical with a conical or frusto-conical inward protrusion from the base thereof to give the reducing internal cross-sectional area which gives rise to the reverse-cyclone flow pattern described previously. Preferably, however, the outer wall of the chamber tapers towards the base. This could be a curved taper, but preferably the shape is generally frusto-conical. This has been found to give the most efficient reverse-cyclone flow pattern.

The chamber including its air inlet will be arranged so that the necessary vortex is set up when a user inhales. Although there are other ways of achieving this, conveniently the air inlet is directed substantially tangentially. Preferably the chamber has a cylindrical section in the region of the air inlet. This facilitates establishment of the free vortex airflow.

In general, the outlet from the chamber will be provided at approximately the same level as or below the air inlet. This maximizes the benefit given by the reverse-cyclone flow pattern.

In accordance with both aspects of the invention set forth above, the powdered drug or other substance could be metered from a bulk reservoir or could be held in individually measured doses. Where the circulation of the cyclone chamber is provided on a replaceable part, it is preferred that one or more doses of the powdered substance is also provided on the replaceable part. This is a particularly advantageous arrangement since it simplifies the provision of the two "consumable" elements that is to say the powdered drug or other substance itself and the chamber which is regularly replaced. Again, in these embodiments the drug or the like could be metered from a reservoir in the replaceable part but it is preferred to provide one or more discrete doses. This simplifies construction which of course allows the production cost of the replaceable part to be minimized and, in accordance with another preferred feature allows the doses to be individually sealed which protects them from contamination, especially by moisture and cross-contamination between used and unused doses.

A removable part for a dry powder inhaler comprising a circulation or cyclone chamber and a quantity of powdered substance for inhalation is clearly an advantageous embodiment of the invention or included in advantageous embodiments. Where a plurality of discrete doses is provided these will of course often be identical to one another. However it is envisaged that in some embodiments it will be beneficial for the doses to vary in size.

One or a plurality of circulation or cyclone chambers may be provided on the replaceable part. A plurality of doses could be associated with each chamber, i.e. so that a given chamber is reused a small number of times, but it is preferred that only a single dose is associated with the or each chamber. Also two or more drug powders could separately stored and mixed in a cyclone chamber e.g. with two or more tangential inlets to the cyclone chamber.

The replaceable part could be provided in general with one or a plurality of circulation or cyclone chambers and one or a plurality of powdered doses. Preferably the chamber and/or chambers is protected by a frangible membrane e.g. a polymeric or metallic foil to protect the formulation against environmental conditions.

Even where the cyclone chamber is not provided on a replaceable part, the drug or other powder could be. This would have the advantages mentioned above of isolation of the drug prior to use etc. In such arrangements, the drug is preferably released by the act of installing the replaceable part to the inhaler. For example, where the drug is stored in a frangible membrane, the inhaler could be arranged to pierce this when the replaceable part is installed.

Although so far only embodiments of the invention in which the entrained particles encounter a single cyclone chamber have been specifically mentioned, this is not essential. Thus, the inhaler could be provided with two or more circulation or cyclone chambers. These could be arranged in series with one another, in parallel with one another or a mixture of the two. An example of the latter would be where two or more parallel ante-chambers feed a single downstream chamber or conversely where a single ante—chamber feeds a plurality of downstream chambers. Of course there are many variants possible depending upon the number of chambers provided. One particular possibility is that one or more cyclone or circulation chambers could be provided on a replaceable part and one or more further chambers provided integrally with the inhaler. For example, the chamber on the replaceable part could act primarily to trap carrier particles which would then be discarded along with the disposable part, with subsequent chambers in the inhaler acting primarily to enhance the de-aggregation or selection of respirable particles.

Returning to storage of discrete pre-metered doses, in some preferred embodiments these could be provided with a second membrane to isolate them from the rest of the interior of the disposable part. This would further enhance the protection against moisture and contamination. This would allow the powder to enter the air stream in a specific region of the airway which may be beneficial to performance. In some preferred embodiments, desiccant means are provided in association with the stored powder dose. One possibility would be to provide desiccant crystals in a physically separate but gaseously communicated pouch. However, a preferred example would be to provide a different layer within a membrane retaining powder.

In accordance with all embodiments of the invention, the dose of powder could be arranged to be introduced into and entrained by the inhaled air at any convenient point in the system. For example, the powder could be stored within the cyclone chamber and released at the appropriate time into the chamber. Alternatively, the powder could be introduced into the cyclone by the vortex finder where such is provided. Preferably, however, the powder is entrained prior to entry into the cyclone chamber. In some preferred embodiments this takes place in the conduit leading to the cyclone chamber, although in an advantageous arrangement a further ante-chamber is provided upstream of the cyclone chamber into which the powder is delivered. Preferably this ante-chamber is arranged to encourage a circulatory airflow therein. This has the advantage of providing a "scouring/scrubbing" flow to collect powder efficiently from the inner surface of the chamber. It is of particular benefit in applications where the powder particles do not flow very well.

Returning to the shape of the tapering area reverse-cyclone chamber, the Applicant has devised a some possible features whereby performance of the chamber may be enhanced. In some preferred embodiments, the base of the cyclone chamber generally conforms to part of the surface of a toroid, which has been found generally to enhance the establishment of the reverse-cyclone flow pattern, but also more particularly to enhance tight local circulation of the larger particles which are trapped at the base of the cyclone chamber.

In another potential preferred feature, the base of the cyclone chamber is provided with a series of concentric ridges i.e. it has a stepped profile. In some circumstances this can give a more desirable flow pattern.

In another potential preferred feature vertical ridges may be provided in the chamber to enhance the performance.

In yet another possibility, the surface finish of the wall of the chamber could be made rough or smooth as desirable to give an appropriate flow pattern. The surface finish could even vary from rough to smooth or vice versa to influence the particular flow since the Applicant has observed that the roughness of the surface affects the performance of the cyclone. Of course, any combination of the features mentioned above may be employed.

Where, as is preferred, the cyclone chamber is protected by a frangible membrane, this is could be pierced upon installation into the inhaler but in at least some preferred embodiments it is preferably pierced by the patient when the dose is ready to be taken. Preferably the outlet pipe projects into the chamber to form a vortex finder.

The dimensions of the inhaler may be chosen to suit the particular desired application. However the features set out herein are especially advantageous in inhalers which can be held in one hand. Preferably the diameter of the cyclone chamber is between 5 and 100 mm, more preferably between 5 and 50 mm and most preferably between 8 and 20 mm.

In another preferred form of the invention, an inhaler includes a tubular mouthpiece, an open casing, a support structure and a drug holder. In this form, the open casing has two sidewalls extending from a top portion and defines an interior region between the sidewalls. The casing includes at least a first port and a second port extending therethrough.

The support structure is disposed in the interior region of the casing and substantially closing the interior region, The support structure includes a base member disposed opposite the top portion and a mouthpiece support member extending therefrom to the top portion.

The mouthpiece support member includes a first airflow guide extending therethrough from the mouthpiece outside said interior region, through said interior region to and through said base member, to a first tubular piercing member extending from said base member to points outside said interior region. The mouthpiece support member further, optionally includes a second airflow guide extending therethrough from said mouthpiece outside said interior region to points inside said interior region. The base member includes a second tubular piercing member extending therefrom to points outside said interior region.

The base member also includes a channel member extending between said base member and said casing, where said channel member defines a first subportion of said interior region and a second subportion, where said first and second subportions are pneumatically isolated from each other. The second subregion pneumatically couples said second port and said second airflow guide, and said first subregion pneumatically couples said first port and said second tubular piercing member.

The drug holder is preferably cup-shaped, having a peripheral edge adapted to support therein a drug container having a planar top substantially alignable with said peripheral edge. The drug container preferably used with the inhaler, includes a first recess and a second recess extending therefrom, which are interconnected by a channel. The drug container has a piercable membrane affixed to its top surface, spanning said recesses and forming first and second chambers. The first and second recesses are alignable with and adapted to receive said first and second piercing members respectively when said drug container is positioned in said drug holder.

The drug holder is pivotally coupled to said support structure and is positionable between (i) a first position wherein said peripheral edge engages said support member and said first and second piercing members extend through the plane of said top of said drug container when said drug container is positioned in said drug holder, and (ii) a second position wherein said drug container can be removed therefrom or inserted therein.

Preferably, the first recess of the drug container is conic frustum-shaped, and most preferably is shaped to establish cyclonic airflow therein in response to inhalation at said mouthpiece by a user.

With said drug container in said drug holder and in response to inhalation at said mouthpiece by a user, airflow is established along a primary airflow path from points external to said inhaler through said first port, said first subregion, said second piercing member, said second recess of said drug holder, said channel interconnecting said first and second chambers, said first chamber, said first piercing member, said first airflow guide, and a first mouthpiece port in said mouthpiece, to points exterior to said inhaler, and optionally, along a secondary airflow path from points external to said inhaler through said second port, said second subregion, and a second mouthpiece port in said mouthpiece, to points exterior to said inhaler.

In a preferred form, said primary airflow path and said secondary airflow path are pneumatically isolated in said inhaler.

For drug therapeutic use, said first chamber of the drug container includes therein a dry powder medicament. Preferably, said medicament includes a particulate drug and a particulate carrier, wherein at least some drug particles are coupled to carrier particles.

In a preferred form, the base member is substantially planar and wherein said first airflow guide extends along an axis substantially parallel to the plane of said base member. In another preferred form, said first airflow guide extends along an axis angularly offset by an angle A with respect to the plane of said base member, where angle A is in the approximate range 30-60 degrees, and most preferably is approximately 45 degrees.

A drug container which is readily used with inhaler, or can be used with other inhalers, has a planar top and including a first recess and a second recess extending therefrom, where the recesses are interconnected by a channel. The drug container has a piercable membrane affixed to said top surface and spanning said recesses forming first and second chambers, where said first and second recesses being alignable with and adapted to receive first and second piercing members respectively when said drug container is positioned in a drug holder of an inhaler. Preferably said first recess is conic frustum, and most preferably said first recess is shaped so that, when said membrane is pierced over said first and second recesses, and a pressure differential is established between said first and second recesses, and the pressure at said first recess is lower than the pressure at said second recess, cyclonic airflow is established in said first recess. In use said first chamber includes therein a dry powder medicament. Preferably, the said medicament includes a particulate drug and a particulate carrier, wherein at least some drug particles are coupled to carrier particles.

BRIEF DESCRIPTION OF THE DRAWINGS

Certain preferred embodiments of the invention will now be described, by way of example only, with reference to the accompanying drawings in which:

FIG. 9 shows the performance test results for the cyclone chambers A-E of FIG. 8 compared to two conventional dry powder inhalers; and FIGS. 10 to 25 show schematically various further possible embodiments of the invention.

DETAILED DESCRIPTION OF THE INVENTION

Figure 1:
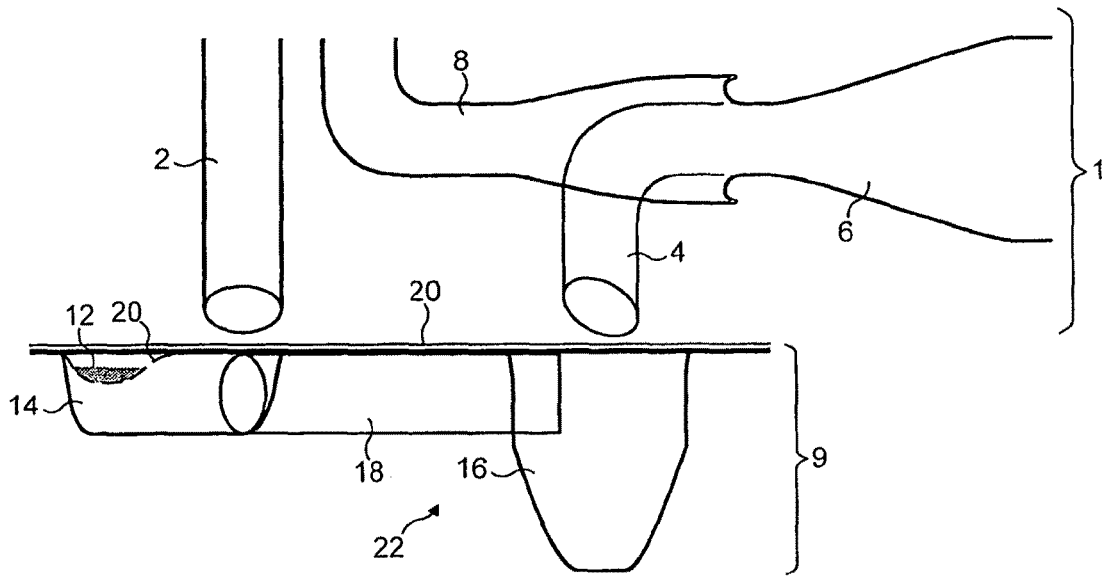
FIG. 1 is a schematic sectional diagram of an inhaler in accordance with the invention.

With reference to FIG. 1, the general construction and operation of a dry powder inhaler in accordance with the invention will be described. Since this and some other Figures are schematic diagrams intended to demonstrate the functional interrelationships of the various elements, they do not necessarily depict the elements in their accurate spatial relationships.

The inhaler is divided broadly into two parts: a re-useable part 1; and a replaceable part 9. The reusable part 1 generally comprises an air inlet tube 2; an entrained-drug outlet tube 4 in fluid communication with a mouthpiece 6; and a bypass air tube 8, also in fluid communication with the mouthpiece 6.

Figure 2:
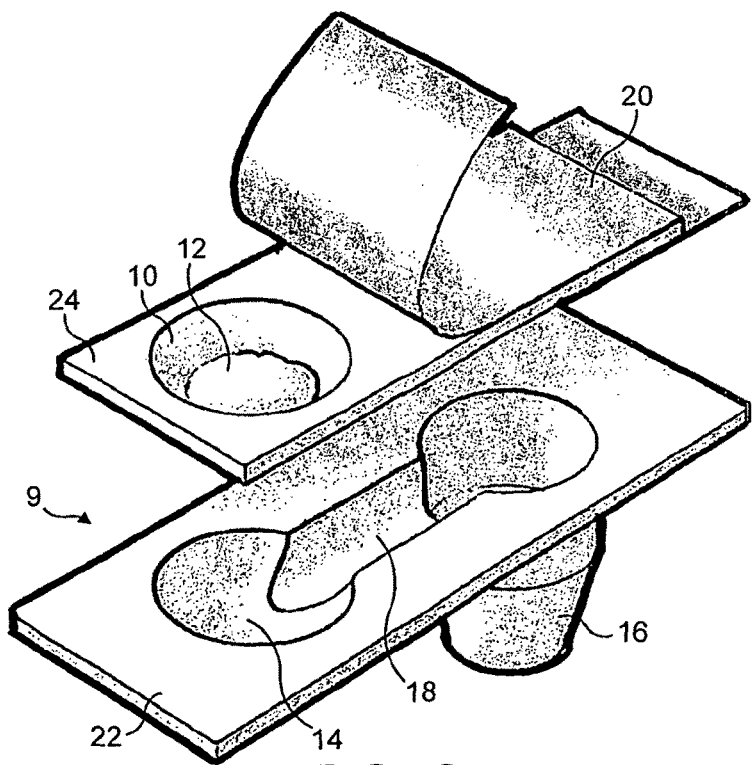
FIG. 2 shows the assembly of the replaceable part of FIG. 1.
Figure 3:
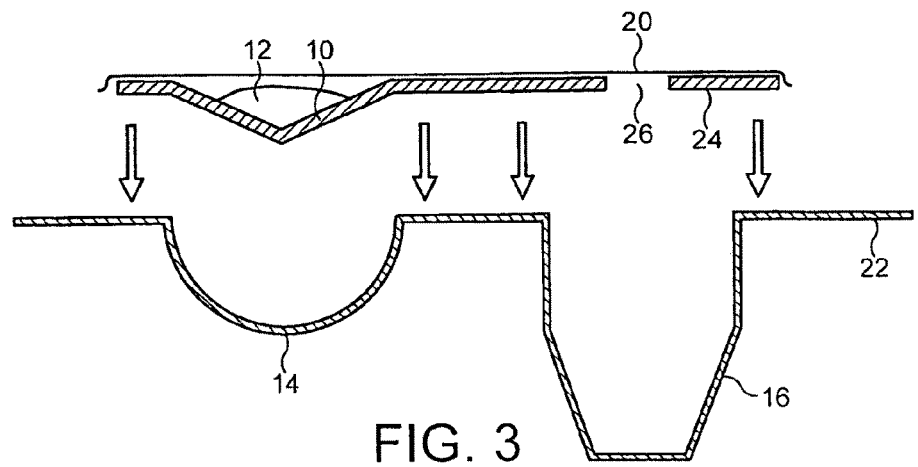
FIG. 3 is a cross-sectional view of the replaceable part of FIG. 2.

The replaceable part 9, is shown schematically, separated from the reusable part, in FIG. 1 and in greater detail in FIGS. 2 and 3. It is made up of a lower body 22, an upper cover part 24 and an overlying foil membrane 20. The lower body 22 could be of plastic material chosen so as to have a low permeability to moisture ingress. Manufactured into the lower part is an approximately hemi-spherical swirl chamber 14 connected by a channel 18 to a frusto-conical cyclone chamber 16.

The upper part 24 is of formed foil shaped to define a pocket 10 lying above the swirl chamber 14 and containing a single metered does of powdered drug. Any form of powdered drug could be used either bound to carrier particles such as lactose or in free powder form. The upper part 24 also defines an aperture 26 overlying the cyclone chamber. An attached foil cover 20 seals across the blister 10 and the aperture 26 to prevent the ingress of moisture.

Operation of the inhaler described above will now be described. It will be appreciated that this is a description of typical operation and will not necessarily apply to all embodiments. To prepare the inhaler for use the user must first install the disposable blister 9 into the reusable part of the inhaler 1. As the blister part 9 is inserted, the foil cover 20 and subsequently the base of the dose pocket 10 are pierced by the air inlet tube 2 as it passes through into the swirl chamber 14, releasing the dry powder dose 12 into the swirl chamber 14. The end of the inlet tube 2 is sharpened to assist clean penetration of the foil. The outlet tube 4 is similarly sharpened so as to penetrate the foil cover through the aperture 26 and pass some way into the cyclone chamber 16.

Figure 4:
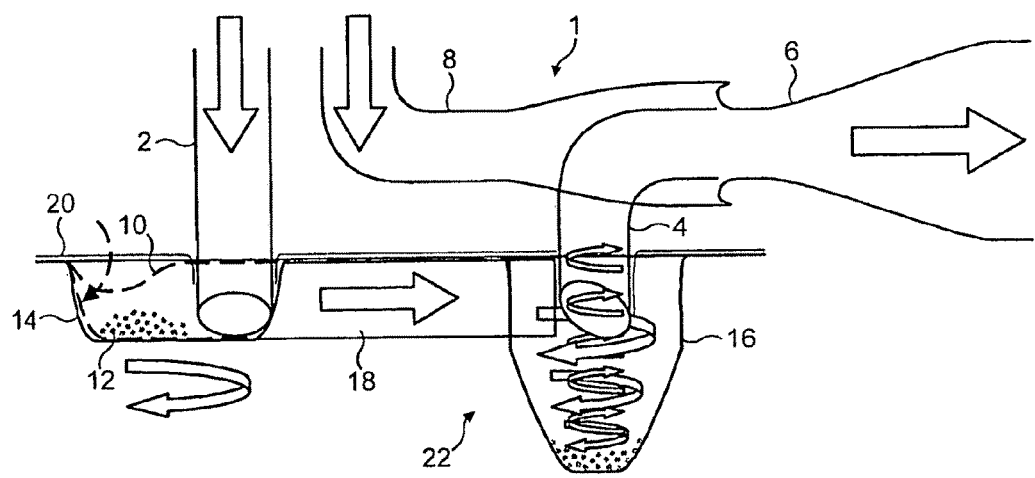
FIG. 4 is a schematic diagram showing operation of the inhaler.
Figure 5:
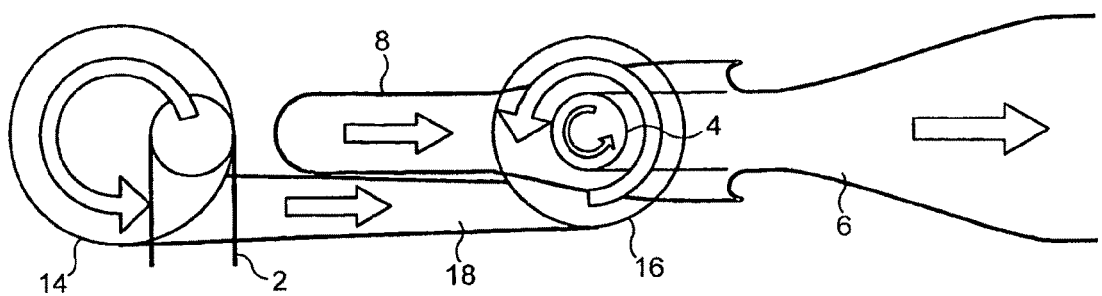
FIG. 5 is a plan view of the air flow shown in FIG. 4.

The user then inhales through the mouthpiece 6, sucking air through both the air inlet tube 2 and the bypass air inlet 8. The air flow through the inhaler is shown in FIGS. 4 and 5. As the inlet tube 2 is offset from the central axis of the swirl chamber 14, air flowing through the inlet 2 enters the chamber 14 tangentially and sets up a swirling "scouring" flow. This helps to ensure that all of the powder dose is cleaned from the chamber. Since the air in this chamber 14 will typically pass several times around the chamber collecting powder, it also helps lengthen the duration of the delivery of drug throughout the inhalation. The flow of entrained particles passes out of the swirl chamber 14 and along the channel 18, which in turn directs the flow tangentially into the upper part of the cyclone chamber 16. The cross-sectional shape and area of the channel 18 at its outlet into the cyclone chamber 16 is chosen so as to promote a well-defined grade efficiency curve in the cyclone chamber 16. This would be optimized on the basis of a specific application.

Figure 6:
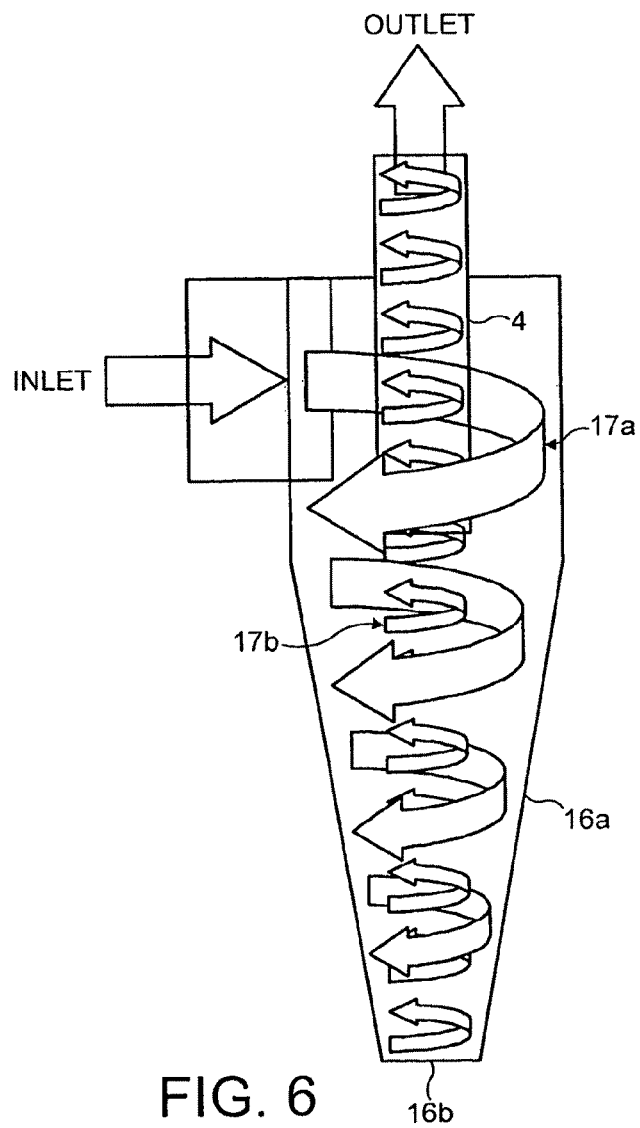
FIG. 6 shows the reverse cyclone airflow in the chamber.

The resulting reverse-cyclone flow pattern in the cyclone chamber 16 is shown in greater detail in FIG. 6. The tangentially entering air and cylindrical upper wall portion set up a bulk circulation of air around the periphery of the chamber 16. The inlet from the communicating channel 18 is also angled down slightly so that the air flow is a shallow downward spiral known as a "free" vortex 17*a*. Due to conservation of angular momentum, the rotational velocity of the free vortex increases as the airflow is constricted by the tapering inner surface of the frusto-conical portion of the chamber 16*a*. As the free vortex 17*a* hits the base of the chamber 16*b* it is reflected to form a tight "forced vortex" inside the free vortex and travelling back up the axis of the chamber.

At the top of the chamber 16 the downwardly projecting end of the outlet tube 4 forms a vortex finder. The vortex finder 4 effectively defines a maximum cut-off circulation radius for entrained particles to exit the chamber. Particles circulating at a radius greater than that of the vortex finder 4 will not escape but will either fall back into the cyclone or fall to the base of the chamber 16*b*.

As entrained powder particles enter the cyclone chamber 16 to be carried downwardly they circulate around the chamber 16 several times. As they travel, the particles experience a shear force arising the from the relatively high spatial velocity gradients that occur when measured across the two vortices 17*a*, 17*b*. This shear force tends to de-aggregate and de-agglomerate the particles so that the average size of the particles is reduced and drug particles circulate separately from carrier particles.

At the base of the chamber the reversal of direction causes the heavier particles, such as the carrier particles to come out of the main flow to be trapped in eddy currents at the bottom of the chamber or simply to sit at the bottom of the chamber. In an alternative embodiment illustrated in FIG. 7, the cyclone chamber 16' comprises a base 28 that is toroidal in shape. This shape enhances the collection of large unwanted particles in the base of the chamber 16 by encouraging them to circulate in eddy currents which traps them in the base so that they cannot be inhaled by the user.

The lighter particles which remain entrained travel back up the chamber 16 in the forced vortex 17*b* giving a further opportunity for de-aggregation. The diameter of the carrier particles is greater than the depth of the boundary layer at the wall of the cyclone chamber and therefore large particles do not remain stationary on the cyclone chamber wall but continue to circulate releasing fine particles throughout the inhalation. It will be seen therefore that in contrast to particles being drawn once round a swirl chamber as is known from the prior art, the flow path obtained in accordance with the invention gives a long path through the chamber and so a long residence time which enhances the de-aggregation efficiency, by increasing the number of opportunities the fine particles have to be removed from the carrier particles. The smaller particles with lower momentum circulate at relatively short radii whereas larger particles with greater momentum circulate at larger radii. At the top of the chamber the vortex finder 4 selects the smaller particles, e.g. those of diameter 5 µm or less, with the rest remaining in the chamber as explained above.

The forced vortex air flow exits the cyclone chamber 16 through the vortex finder 4 and passes along the mouthpiece 6 into the mouth of the user. The diverging mouthpiece 6 slows the air flow before it enters the mouth of the user so that it does not impinge forcefully against the back of the user's throat. The bypass air flow through the inlet 8 is directed along the inner wall surface of the mouthpiece 6 thereby creating a sheath airflow through the Coanda effect so reducing the likelihood of powder deposition on the inner surface. By surrounding the air exiting the chamber 16, the bypass air also helps to reduce its residual circulation velocity.

The main function of the bypass air flow through the inlet 8 however is to limit the air flow through the cyclone. If the whole of the breath were to be drawn through the cyclone chamber all of the particles would have a greater velocity and therefore a larger circulation radius and for a given cut-off size (e.g. 5 μm) the diameter of the vortex finder would have to be larger too, in order to allow respirable particles to escape This would require a cyclone chamber too large for incorporation in a convenient hand-held device. Moreover the bypass air inlet can help to limit the variation in the air flow through the cyclone chamber 16 when the rate of inhalation varies. If the rate of inhalation increases, the bypass air flow also increases, which limits the increase in the air flow in the cyclone and so the tendency for the cyclone to become too efficient, i.e. for the particle cut-off diameter to become too low to deliver the full dose.

The form and dimensions of the bypass air inlet 8 is designed to set the inhaler overall resistance and the proportion of an average breath air flow which passes through the cyclone relative to the bypass air flow. In further embodiments (not shown) the bypass air inlet can include a variable resistance valve such as a resilient star valve which reduces in resistance as air flow through it increases so as substantially to maintain air flow through the cyclone chamber constant. Alternatively, one or more resiliently biased flaps may be provided in the bypass air flow pipe 8, the extent of opening of the flaps increasing with an increasing rate of inhalation.

By the time the powdered drug enters the user's respiratory system it will generally contain a high proportion of particles of 5 λm or less (i.e. a high Fine Particle Fraction). These can be inhaled into the deep part of the lungs where they will be most effective. Furthermore very little of the drug or carrier is deposited on the back of the user's throat which is beneficial medically and from the point of view of user comfort.

EXAMPLES

Figures 7, 8:
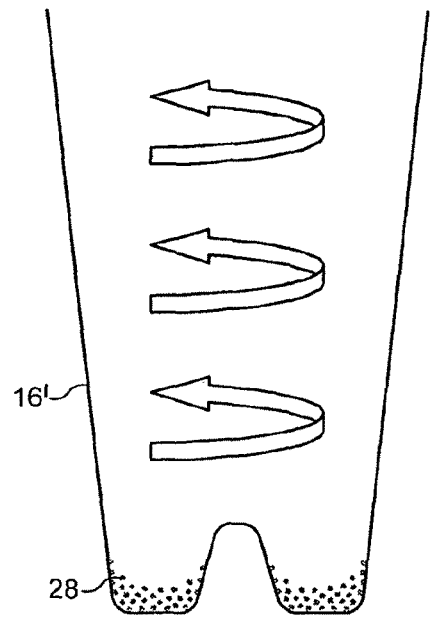
FIG. 7 shows an alternative embodiment of the cyclone chamber with a toroidal base.
FIG. 8 shows five different cyclone chamber configurations A-E used to test the performance of a reverse flow cyclone.

FIG. 8 shows five different cyclone chamber configurations A-E used in a performance test. The cyclone chamber diameters range from 10 to 20 mm. FIG. 9 shows the performance test results for the cyclones A-E compared to two conventional dry powder inhalers. The fine particle fraction achieved using the cyclones A-E is seen to be over 69%, and as much as 81%, compared to only 30-40% for conventional dry powder inhalers. This results from the deposition of large particles above the cut-off size in the base of the cyclone chamber, so that the fine particle fraction is greatly enhanced. The size of the particles separated by the cyclones A-E was also reduced to 2-3 μm in all configurations. Thus cyclone chambers of these configurations separate out particles of a much finer, respirable size than can be achieved by conventional dry powder inhalers, therefore concentration of fine particles in the emitted dose is increased compared to the conventional formulation.

FIG. 10 shows an inhaler reusable part 11 for use with a disposable blister 9 as previously described with reference to FIGS. 2 and 3. The reusable part 11 is comprises two hinged portions, the lower of which defines an inner compartment 30 into which the disposable blister 9 can be fitted. A pair of collars is provided in the compartment 30 to receive the swirl and cyclone chambers 14,16 and so positively locate the blister 9. The upper portion has an inner surface ha which confronts the top of the blister 9 and from which the sharpened ends of the inlet and outlet tubes 2,4 project. To use the inhaler the main body 11 is hinged open to fit the blister 9 into the compartment then closed to pierce the blister ready for inhalation. After use, the inhaler can be opened and the used blister discarded.

Figure 11:
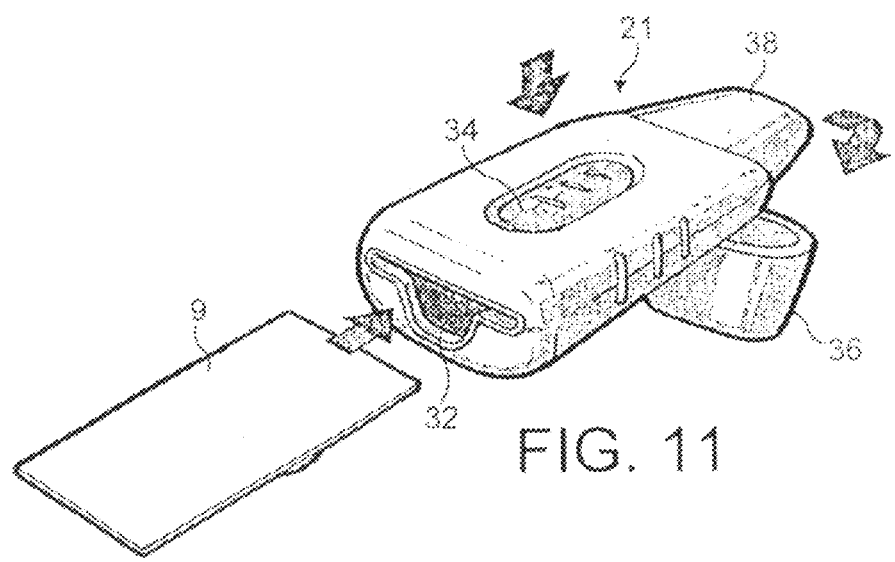

In another embodiment shown in FIG. 11, a disposable blister 9 is pushed into an main body 21 through a slot 32. In this embodiment the blister 9 can be slotted into the inhaler body 21 ready for use but without its foil cover being pierced, so that the inhaler 21 storing the blister 9 can be carried by the user until required, without exposure and contamination of the contents of the blister 9. When a user is ready to take a dose, the blister 9 can be pierced and so connected to the necessary parts of the inhaler 21 by depressing a button 34. The user opens the mouthpiece cover 36 and inhales through the mouthpiece 38. Closing the mouthpiece cover 36 back over the mouthpiece 38 could in some embodiments cause the used blister 9 to be ejected from the inhaler 21.

Figure 12:
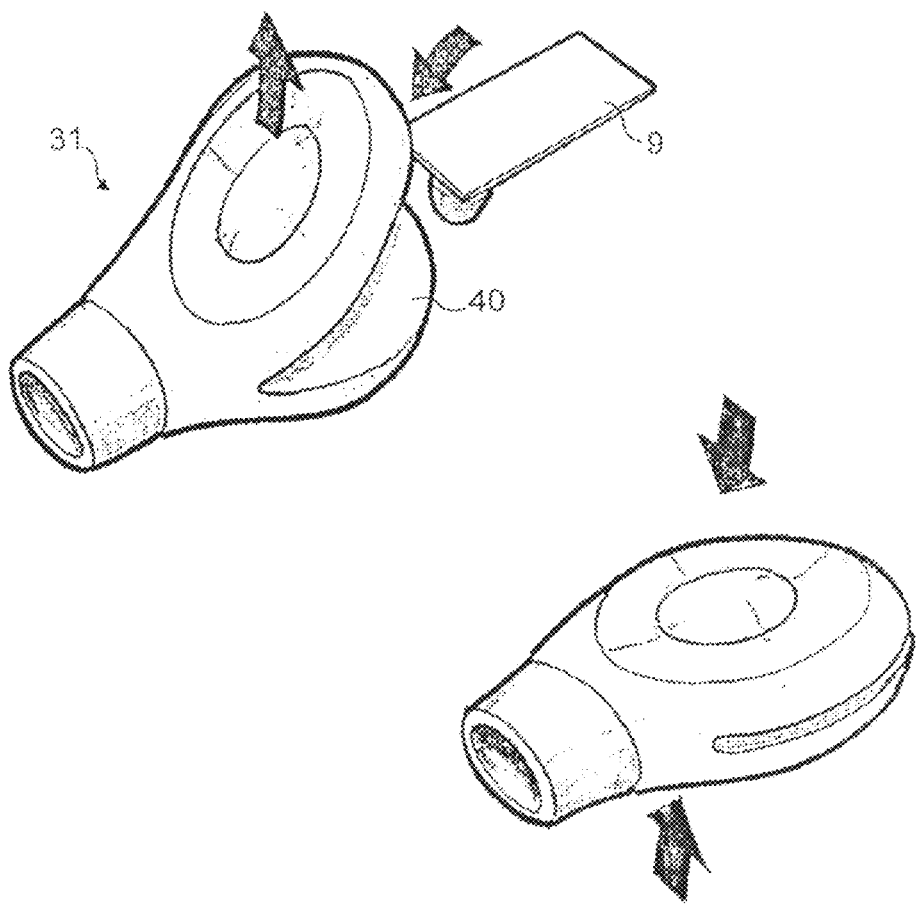

In a further embodiment, shown in FIG. 12, the disposable blister 9 is fitted into an inhaler body 31 which comprises a body 40 made of flexible plastics material. The body 40 is hinged such that it can be flexed open to fit the blister 9, and then squeezed closed to pierce the blister 9 ready for use. The resilience of the plastics body 40 maintains a fluid connection between the inhaler 31 and the pierced blister 9 inside.

With reference now to FIGS. 13 to 17, it will be appreciated that it may be advantageous to fit a cartridge comprising a plurality of separate sealed blisters to an inhaler, so that a user does not have to fit a separate disposable blister each time that a dose is required.

Figure 13:
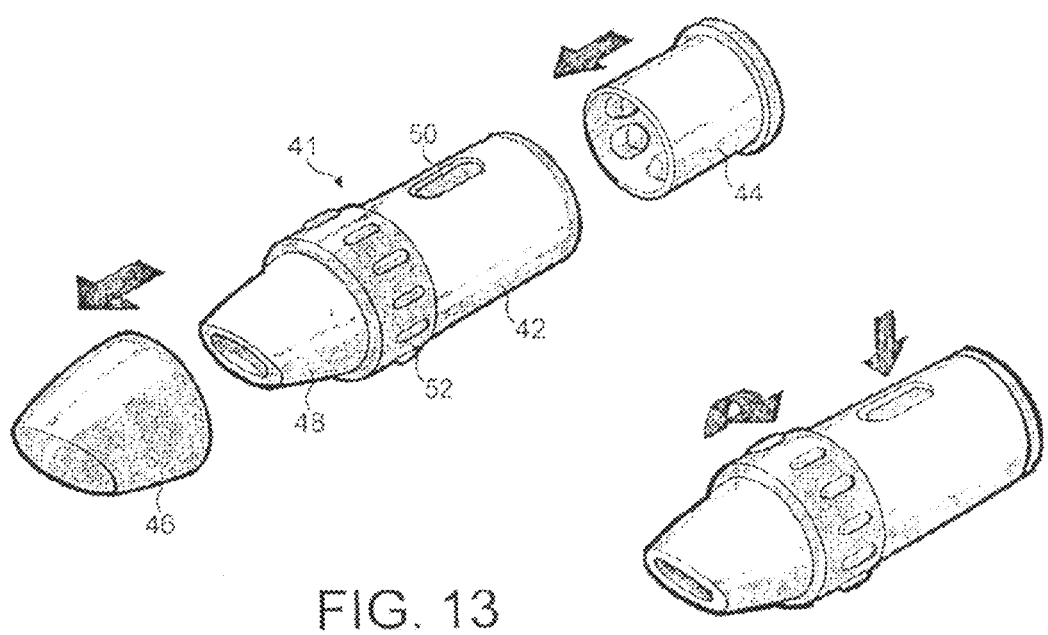

FIG. 13 shows such an inhaler 41 with a main barrel 42 into which may be inserted a cylindrical cassette 44 comprising a circumferentially—spaced array of individual blisters each with a structure similar to that described with reference to FIGS. 2 and 3. The inhaler 41 therefore usefully stores a number of sealed blisters. To use the inhaler 41a user removes the mouthpiece cover 46 ready to inhale through the mouthpiece 48. Depressing a button 50 on the barrel 42 of the inhaler 41 pierces one of the blisters so that its dose can be inhaled. After use the cartridge is advanced by rotating a ring 52 that engages the cassette 44 so that an unused blister is rotated into position beneath the button 50. The inhaler is then primed ready for further use. Once all the blisters in the cartridge have been used, the cartridge 44 can be removed and replaced.

Figure 14:
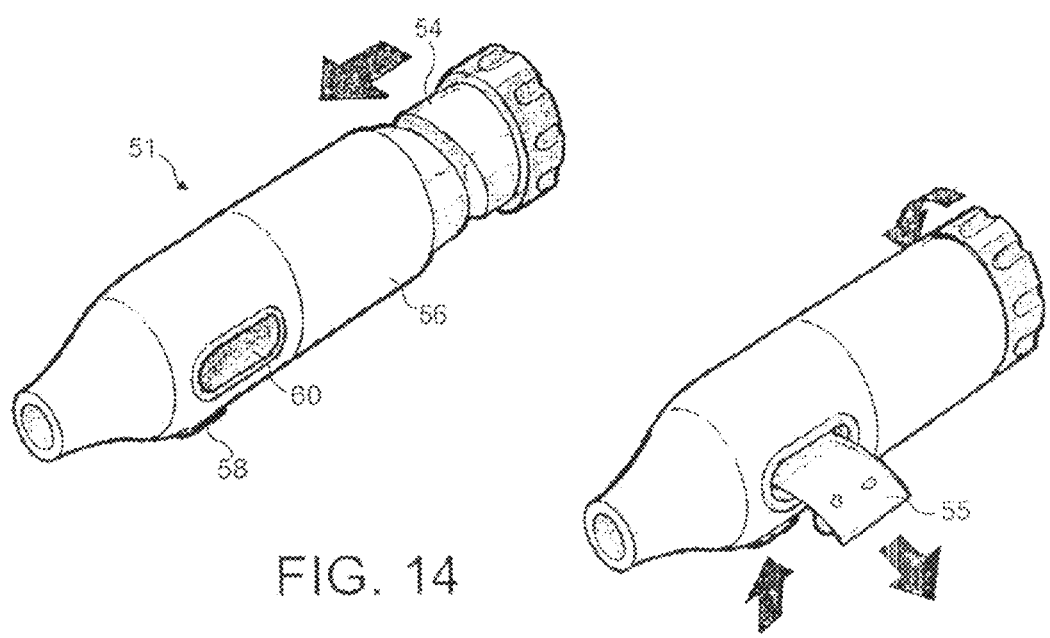

FIG. 14 shows an alternative arrangement in which an inhaler 51 comprises a rotatable cap 54 which advances a coiled strip of blisters 55 stored within the barrel 56 of the inhaler 51. The blister registered for next use is pierced by depressing a button 58 on the underside of the barrel 56 prior to the user inhaling. The end of the strip 55 with the used blisters is ejected through a slot 60 in the barrel 56 and can be torn off.

Figure 15:
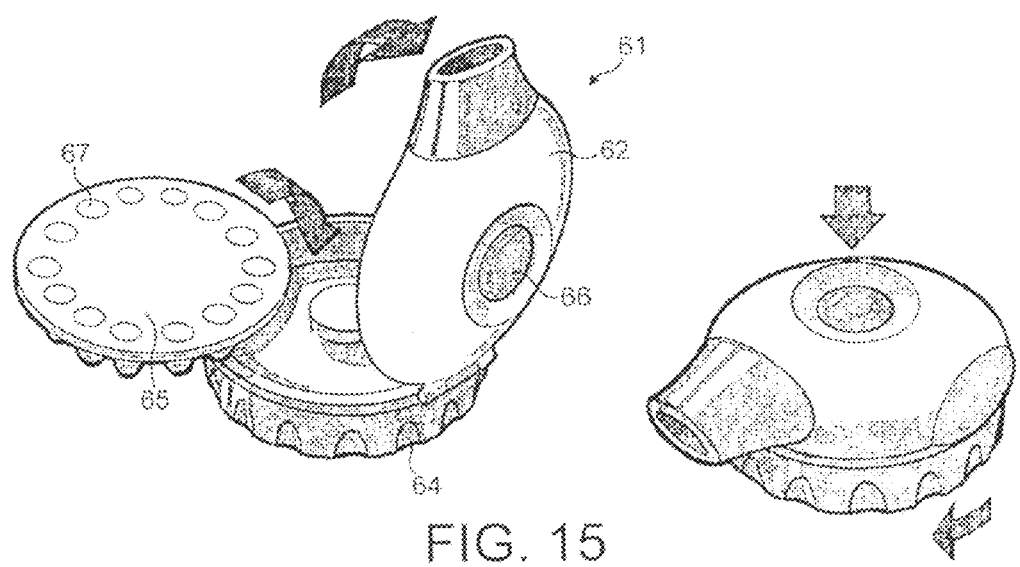

FIG. 15 shows an inhaler 61 and a blister cartridge 65 in the form of a disc. The lower body of the cartridge disc 65a can be seen more clearly in FIG. 17. The disc 65 comprises a plurality of circumferentially-spaced separately sealed blisters 67. The body of the inhaler 61 is hinged so that it can be opened to fit a disc cartridge 65 between the upper 62 and lower 64 parts and then closed to hold and store the disc cartridge 65. A blister is activated by depressing a button 66 on the upper part of the inhaler 62 which pierces the foil cover in the manner previously described. When a particular blister is used, the cartridge can be advanced by rotating the lower part of the inhaler 64 to bring a fresh blister into registry with the inlet and outlet tubes (not shown).

Figure 16:
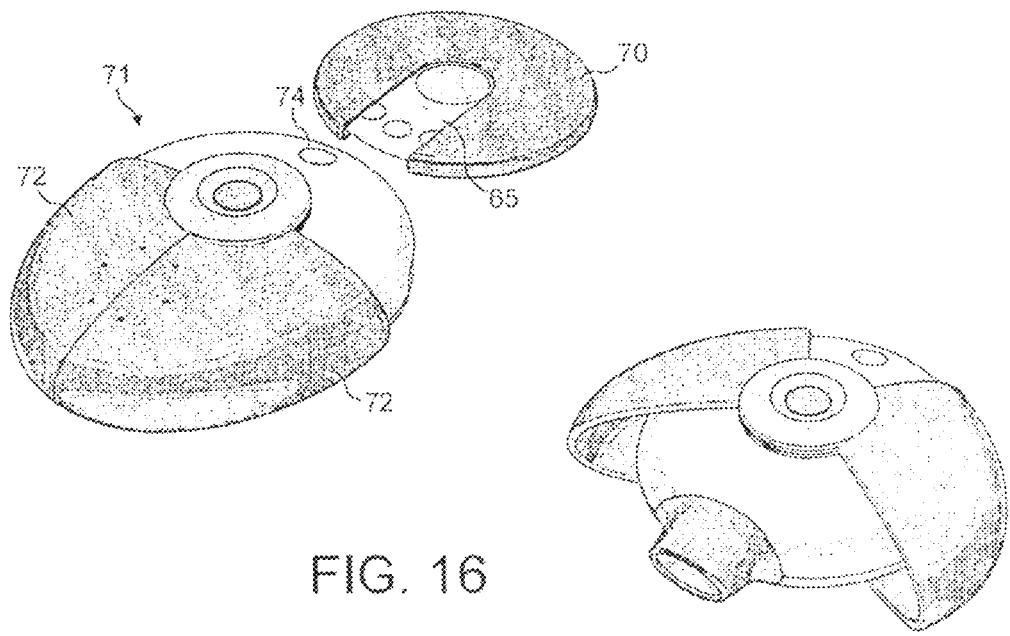
Figure 17:
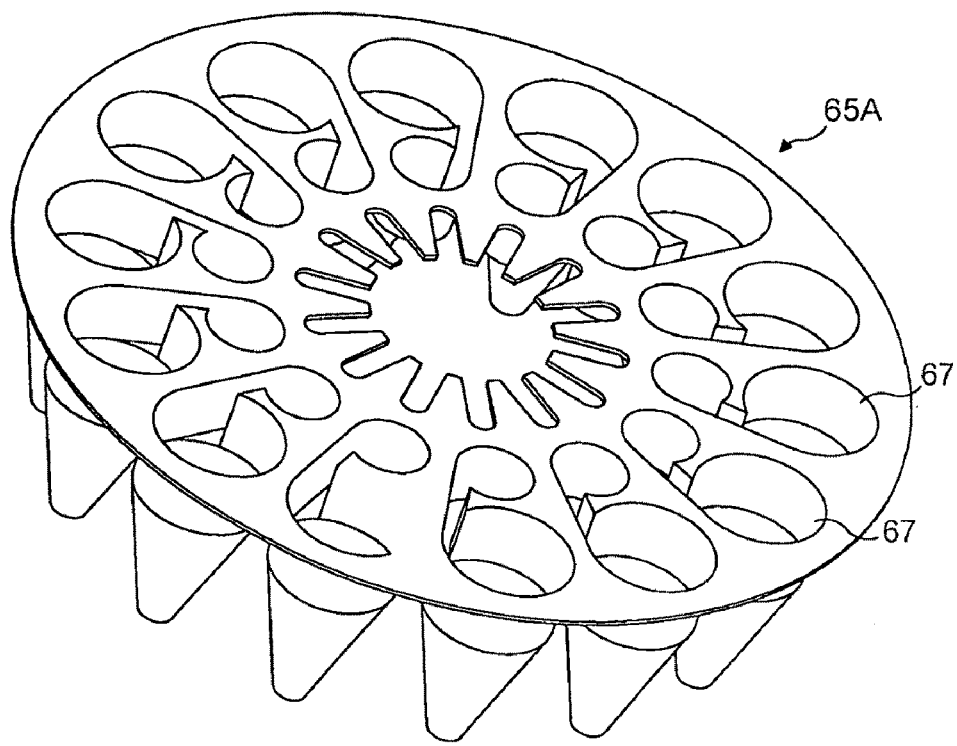

In FIG. 16, another arrangement is shown in which a disposable disc cartridge 65 is contained in a cassette 70. The cassette 70 and cartridge 65 are inserted together into an inhaler body 71. Before each use, the two halves of the mouthpiece cover 72 are rotated back, thereby advancing the cartridge 65 within the cassette 70 to expose an unused blister. The new blister is then pierced by depressing a button 74 on the inhaler 71 ready for inhalation. The advantage of the separate cassette 70 for containing the cartridge 65 within the inhaler 71 is that only one blister is exposed for use at any time. After the blister has been used, it is rotated round into the cassette 70 and therefore isolated from the inhaler 71 so that any waste powder left in the blister cannot contaminate a new dose from another blister. This is particularly important when drug particles remain in the blister, and could potentially affect the dose from another blister.

Figure 18:
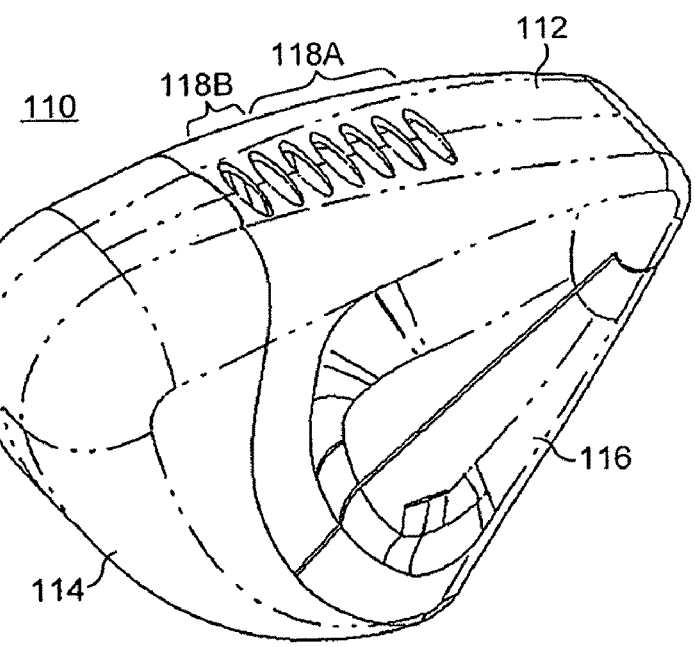

A further embodiment of the invention is shown in FIGS. 18-24. In FIG. 18, a dry powder inhaler 110 is shown having an outer casing 112, a hinged mouthpiece protector 114, and a dose holder 116. The illustrated casing 112 includes seven air inflow ports, five denoted by reference numeral 118A and two denoted by reference numeral 118B. As with the above described embodiments, the inhaler 110 is adapted to dispense dry powder drug/medicament along a main airflow path (MP) extending from ports 118A, through a first piercing tube 124 (not shown in FIG. 18), a foil-faced dose container 122 (not shown in FIG. 18), a second piercing tube 120 (not shown in FIG. 18), and a drug port 126 in a mouthpiece 128 (not shown in FIG. 18) positioned beneath the mouthpiece protector 114. A secondary bypass airflow path (SP) within the casing 112 extends from ports 118B directly to a bypass port 130 (not shown in FIG. 18) in mouthpiece 128. In alternative embodiments, there is only the primary airflow path, without any secondary airflow path.

Figure 19:
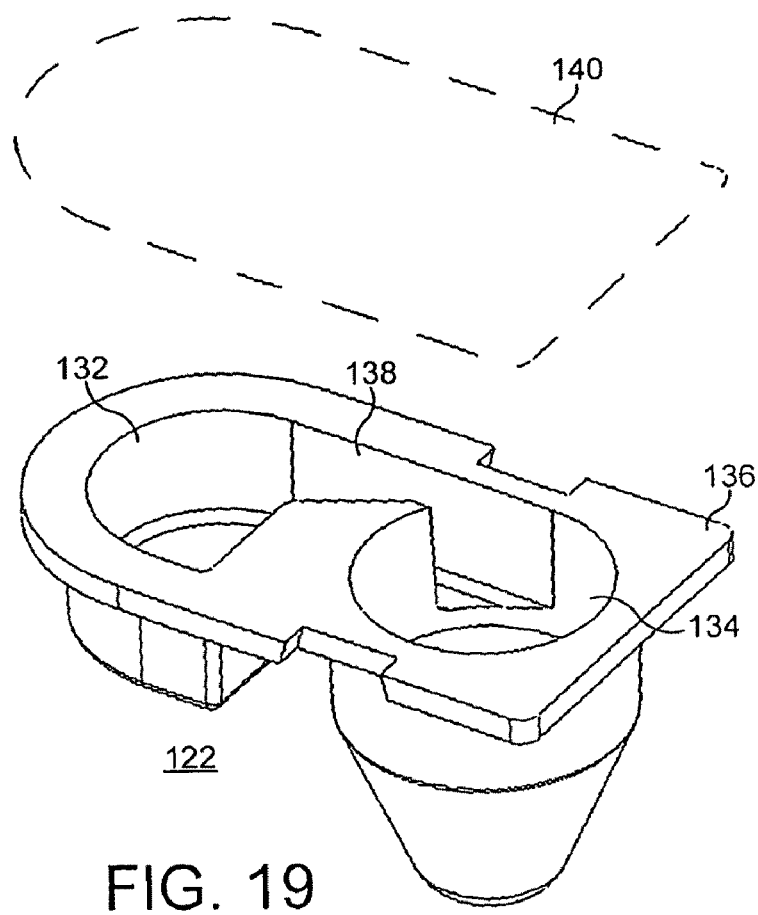
Figure 20:
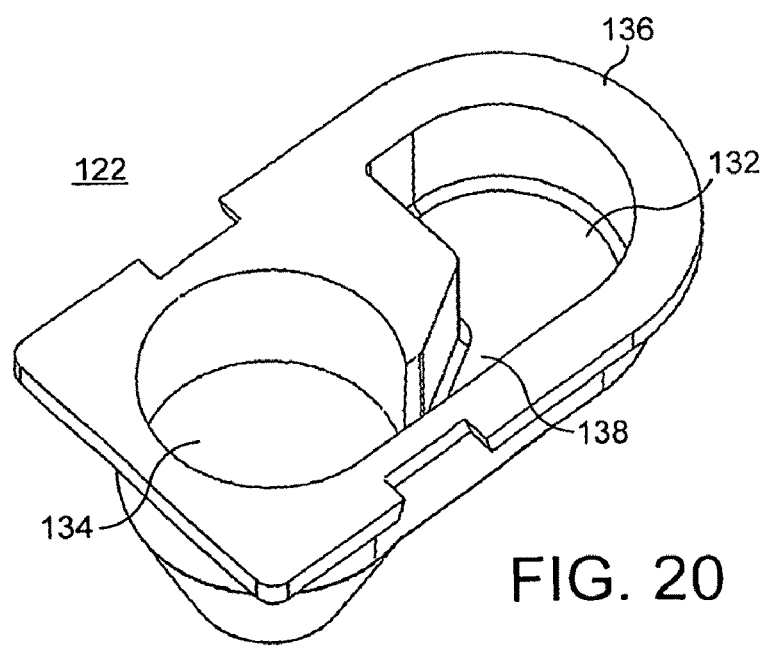

The dose container 122 is shown (without its foil facing) in FIGS. 19 and 20, although the foil-facing is shown in phantom in FIG. 19 displaced from and above the main portion of dose container 122. The dose container 122 is preferably made from a moulded plastic and includes an inlet chamber 132 and an outlet chamber 134 extending from a planner face member 136. A channel 138 interconnects chambers 132 and 134. A piercable foil-facing or laminate 140, shown in phantom in FIG. 19, and not shown in FIG. 20, is affixed to face member 16 and spans and hermetically seals the chambers 132 and 134. The inlet chamber 132 serves as a reservoir for dry powder medicament-to-be-dispensed. The outlet chamber 134 serves as a deagglomerating airflow guide, adapted to effect a separation of relatively small medicament drug particles from relatively large carrier particles entrained in air flow along path MP in use. Preferably, but not necessarily, the chamber 134 is shaped to establish "cyclone" airflow and drug/carrier separation, as described above in conjunction with FIGS. 4-7. The dose container 122 is shaped to removably interfit within the dose holder 116.

Figure 21:
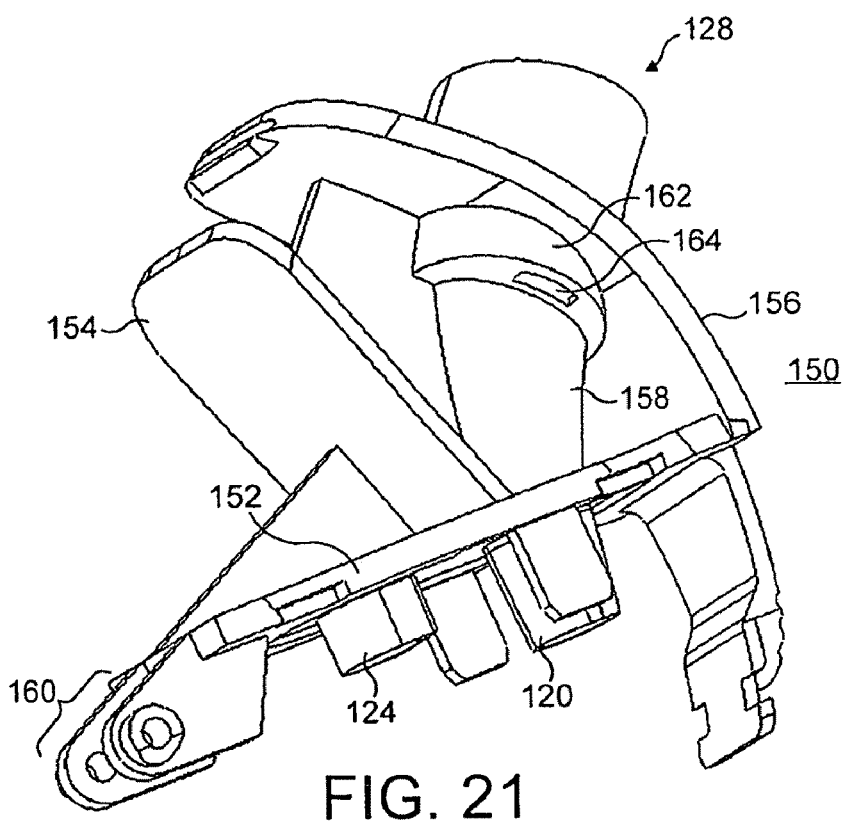

The casing 112 houses a piercer/mouthpiece structure 150, shown in FIG. 21. The structure 150 includes a base portion 152 from which an MP/SP channel divider 154 extends to an inner-surface of the casing 112, between the ports 118A and 118B. The structure 150 also includes a mouthpiece support member 156 extending therefrom, which supports the mouthpiece 128. A MP channel member 158 extends between the support member 156 and the base portion 152, and defines therein a portion of the main air flow path MP between the mouthpiece 128 and the first piercing tube 120, which extends downward (as shown in FIG. 21) from base portion 152. The second piercing tube 124 also extends downward (as shown in FIG. 21) from base member 152. A pivot assembly 160 for pivotally supporting the dose holder 116 with respect to the support 150, extends from the leftmost (as shown in FIG. 21) portion of the base member 152. A collar portion 162 extends about the MP channel member 158 at the junction of MP channel member 158 and mouthpiece support 156. The collar portion includes a first SP port 164 on one side of MP channel member 158 and a second SP port 166 (not shown in FIG. 21) on the other side of channel member 158. The first and second SP ports 164 and 166 couple ports 118B and the region bounded by casing 112, MP/SP channel divider 154 and mouthpiece support 156, to respective ports 130A and 130B (not shown in FIG. 21) of the secondary port 130 of mouthpiece 128. In embodiments not including a secondary air flow path, ports 164 and 166, 130A and 130B are not present.

Figure 22:
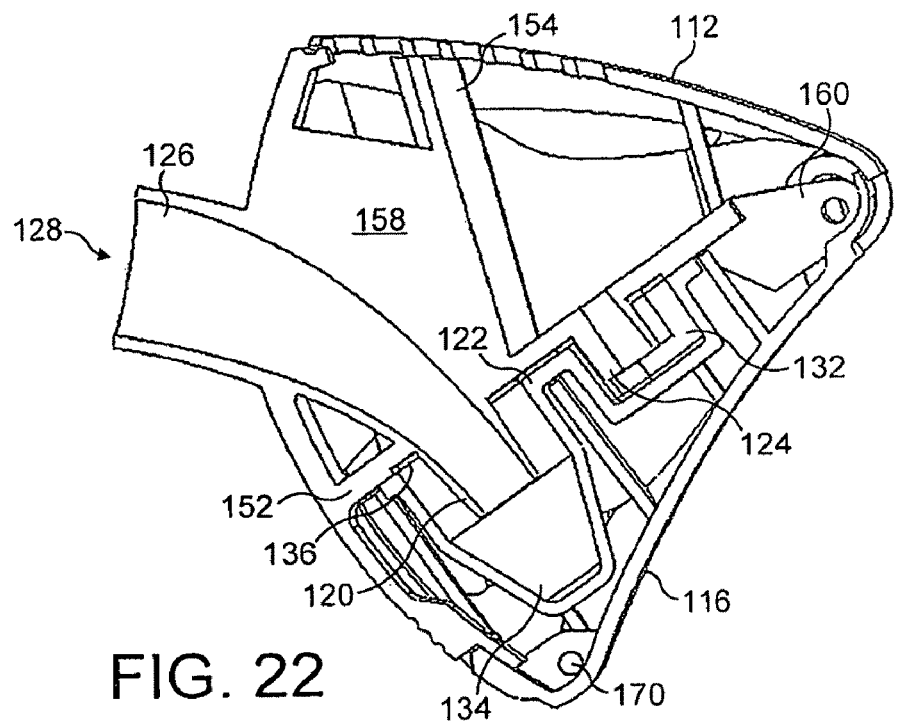
Figure 23:
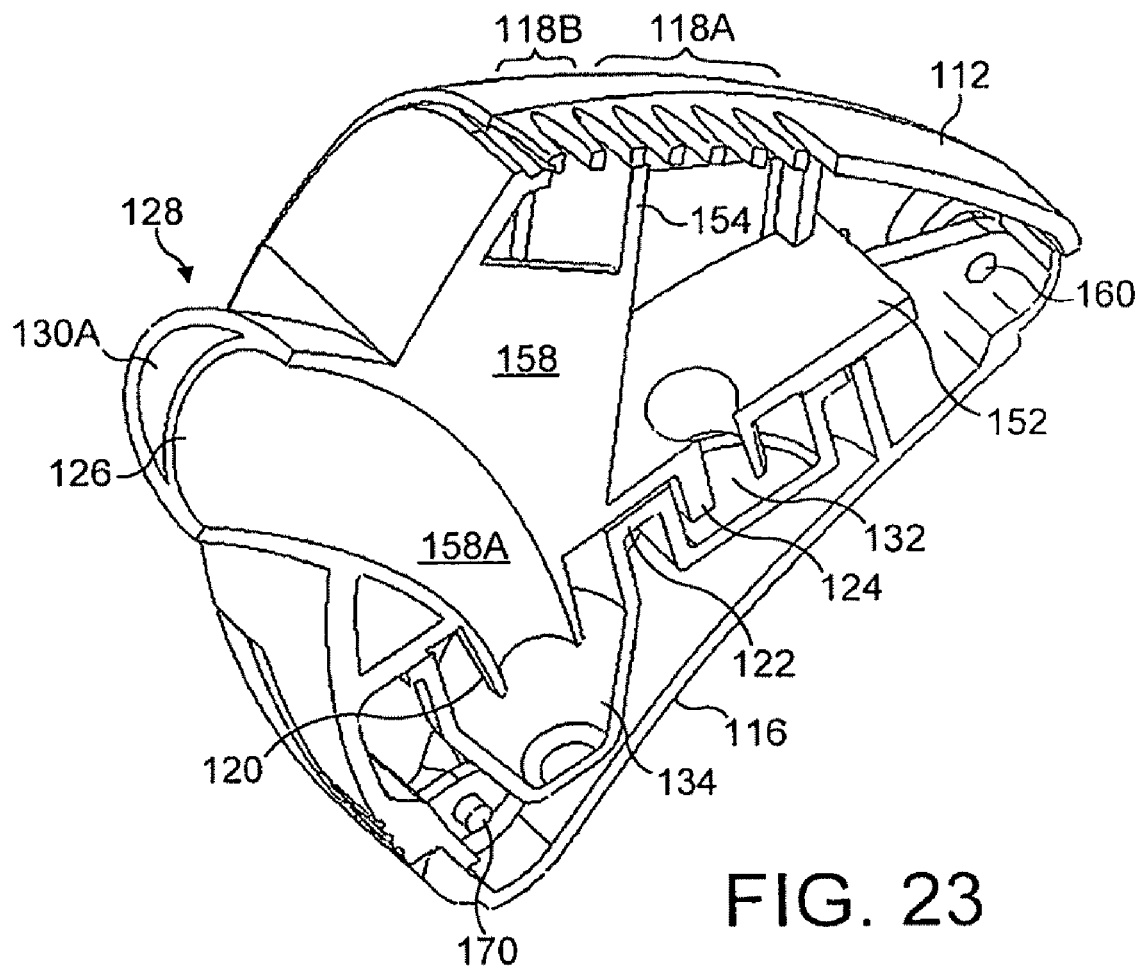
Figure 23A:
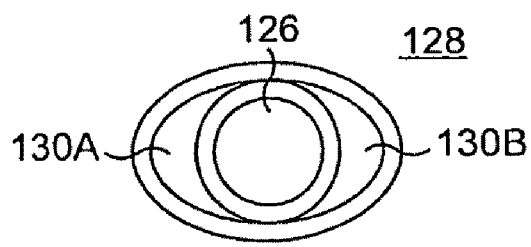

FIGS. 22 and 23 show a sectional view (about a centre plane) and in perspective, (about a centre plane) of the dose holder 116, operatively connected to the pivot assembly 160 of the structure 150. In those figures, the dose holder 116 is fully rotated toward base portion 152 and supports dose container 122 with its face member 136 flush against the underside (as shown in FIG. 23) of base portion 152. In this position, the piercing tubes 120 and 124 are shown as pierced through the foil 140 affixed to face member 136. In this position of dose holder 116 and structure 150, the main flow path MP is established, as described below. The drug container 122 may be removed or replaced by pivoting the dose holder 116 counterclockwise (as shown in FIG. 22) with respect to structure 150, to permit clearance for removing and replacing drug container 122. A pivot assembly 170 (for pivotally supporting the mouthpiece protector 114) is disposed at the left (as shown in FIGS. 22 and 23) end of dose holder 116. FIG. 23A shows a plan view of the mouthpiece 128, showing ports 126, 130A and 130B.

Figure 24:
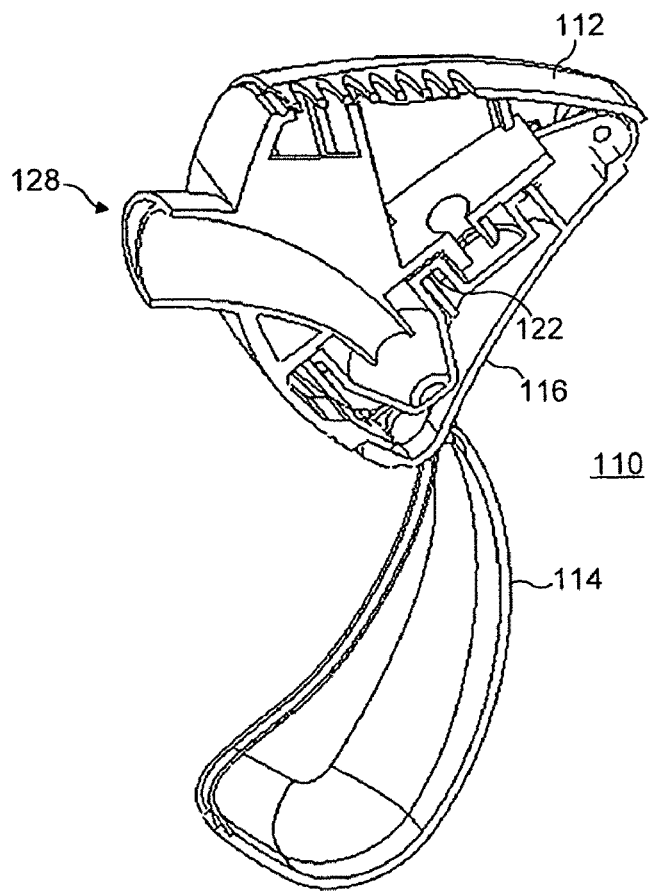
Figure 25:
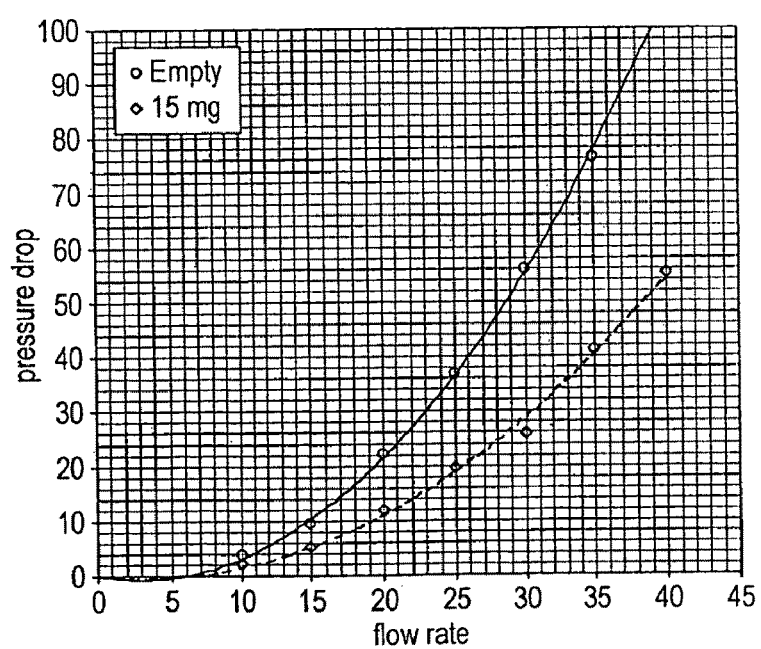

FIG. 24 shows inhaler casing 112, drug holder 116, and drug container 122 as shown in FIGS. 22 and 23, and further shows the mouthpiece protector 114 in its open and ready-to-use position, pivoted counterclockwise (as shown in FIG. 24) relative to drug holder 116. When the inhaler 110 is not in use, it is preferred that the mouthpiece protector 114 is rotated clockwise to a closed position (as shown in FIG. 18) with respect to drug holder 116. In a preferred form of inhaler 110, the mouthpiece protector 114 is resiliently biased toward, or snap fitable to, its closed position, and the drug holder 116 is resiliently biased toward, or snap fitable to, its closed position, for convenience of a user.

In the use of the inhaler 110, a user preferably carries the inhaler 110 in its closed position (as shown in FIG. 18), with the mouthpiece protector in position over the mouthpiece and the drug holder in its closed position, and the user has with him or her, and a ready supply of at least one drug container 122. In order to take a dose of drug, the user pivots the mouthpiece protector 114 to its open position and pivots the drug holder 116 to its open position. The user then inserts a drug container 122 (with its foil 140 intact) into drug holder 116. The user then pivots the drug holder 116 to its closed position. This action causes the piercing tubes 120 and 124 to pierce the foil 140 and enter chambers 134 and 132 respectively. The pivoting of drug holder 116 to its closed position establishes the airflow path MP, from ports 118A, through piercing tube 124, chamber 132, channel 138, chamber 134, the interior 158A of channel member 158, to port 126 of mouthpiece 128. The secondary flow path SP exists at all times from ports 118B to ports 130A and 130B of mouthpiece 128, as described above.

The user then places his or her lips about the mouthpiece 126 and inhales through his or her mouth. As a result, the user establishes a primary air flow along the main flow path MP. In chamber 132, drug and associated carrier particles are entrained into the primary airflow. As the airflow passes by way of channel 138 into and then through the chamber 134, the drug/carrier particles deagglomerate, leaving the carrier particles in chamber 134, while the drug particles travel along the main airflow path MP through the interior 158A of channel member 158 to port 126 of mouthpiece 128, and into the user's mouth. At the same time, outside air is drawn through parts 118B to form a secondary airflow directly to ports 130A and 130B of mouthpiece 126. In this enhancement, the MP path and the SP path are totally separate within the inhaler 110. In some forms of the invention, either or both of the MP and SP path may include flow adjusters, which can effect a desired pneumatic impedance along the respective paths as desired. In various forms of the inhaler 110, other geometries for deagglomeration may be used, which may or may not be of the "cyclone" type.

In cases where no cyclone configuration is used, the drug holder may have two interconnected chambers, as described above, or it may incorporate only a single chamber, with both piercing tubes adapted for entry into the single chamber. Preferably, in this case, the chamber is elongated, and may include a vortex-inducing geometry between opposite ends of the chamber.

In some forms of the invention, a sprung valve is used in the secondary flow path so that a low flow rates, a relatively high proportion of total (i.e. primary and secondary) air flows through the primary path, and through the cyclone chamber, keeping airflow through the cyclone relatively constant. Again, in some embodiments, there is no secondary airflow.

It will be appreciated by those skilled in the art that the embodiments set out above give simple and convenient arrangements for dry powder inhalers in which particles which are too large are retained in the device thus raising the Fine Particle Fraction of what is inhaled and reducing the problems arising with inhaling particles which are too large. This provides significant benefit to the user in a commercially attractive package. Some key features of the preferred embodiments include the following. Firstly, a reverse-flow cyclone to efficiently de-aggregate the respirable (fine) drug particles from coarse carrier fraction (e.g. lactose). This is achieved by increasing the residence time of the particles (therefore a greater number of opportunities for separation), and by maximizing the shear forces for a given energy input. Secondly, the reverse-flow cyclone separates and retains the coarse carrier fraction—i.e. only respirable (fine) drug particles are emitted upon inhalation. Thirdly the use of bypass airflow to control the separation efficiency of the reverse-flow cyclone, and to tailor the airflow resistance of the device.

Fourthly the cyclone geometry being on a disposable component, to maximize Dose Content Uniformity (DCU), by preventing carry-over of drug particles between doses.

Fifthly, formulation is pre-metered into moisture-proof blister, therefore accurate dose mass, and performance independent of environmental conditions. Finally, a disposable blister which retains the non respirable fraction aerodynamically during inhalation and mechanically after inhalation.

However these embodiments are only examples of the large number of possible implementations of the invention and many variants and alternatives are possible. For example it is not essential for the cyclone chamber to be provided on a disposable part—the inhaler could be made as an integral unit whilst still retaining many of the benefits of the invention, particularly those pertaining to the provision of a reverse-cyclone with a bypass air

The invention claimed is:

1. A dry powder inhaler comprising:

a main airflow path including a reverse flow cyclone chamber in which in use air and entrained substance particles circulate, said chamber comprising an axis and being elongate along said axis, an air inlet, a closed base and a vortex finder, said chamber being so shaped that at least a part of the chamber decreases in cross-sectional area in an axial direction away from the air inlet, wherein the air inlet is arranged to direct air so that it circulates about the axis around the periphery of the chamber, and the vortex finder being arranged such that air exits therethrough after a reversal of axial direction at the base of the chamber to set up a reverse flow cyclone in the chamber in which air circulates in two generally concentric overlapping columns in opposite axial directions; and wherein the vortex finder is arranged such that the entrained substance particles which are smaller than a predetermined size exit the chamber but the entrained substance particles which are larger than the predetermined size are retained in the chamber;

the inhaler further comprising a bypass airflow path bypassing the cyclone chamber;

wherein the main and bypass airflow paths communicate with a mouthpiece.

2. An inhaler as claimed in claim 1, further comprising means for varying the flow resistance of the bypass air flow path.

3. An inhaler as claimed in claim 1, wherein the bypass airflow is arranged to surround the air which has passed through the cyclone chamber.

4. An inhaler as claimed in claim 1, further comprising a drug holder pivotally coupled to the inhaler.

5. An inhaler as claimed in claim 4, wherein said drug holder is cup-shaped.

6. An inhaler as claimed in claim 1, further comprising a tubular piercing member, wherein said piercing member projects into the cyclone chamber to form the vortex finder.

7. An inhaler as claimed in claim 1, wherein the cyclone chamber is provided by a removable part.

8. An inhaler as claimed in claim 7, wherein said removable part comprises a plurality of said cyclone chambers.

9. An inhaler as claimed in claim 7, wherein said removable part further comprises a circulation chamber.

10. An inhaler as claimed in claim 7, wherein the removable part comprises a first recess and a second recess, each recess being covered by a frangible membrane or respective frangible membranes.

11. An inhaler as claimed in claim 10, wherein a frangible membrane spans both said first recess and said second recess.

12. An inhaler as claimed in claim 10, wherein the frangible membrane or one of the frangible membranes is pierced by a user when the dose is ready to be taken.

13. An inhaler as claimed in claim 10, wherein said first recess and said second recess are interconnected by a channel.

14. An inhaler as claimed in claim 10, wherein said first recess comprises a circulation chamber and said second recess comprises said cyclone chamber.

15. An inhaler as claimed in claim 7, wherein said removable part comprises one or more doses of a powdered substance which are released by the act of installing the replaceable part to the or an inhaler.

16. An inhaler as claimed in claim 15, wherein desiccant means are provided in association with the stored powder dose(s).

17. An inhaler as claimed in claim 1, wherein said cyclone chamber comprises an outer wall and a base, and wherein the outer wall tapers towards the base.

18. An inhaler as claimed in claim 1, wherein said cyclone chamber is generally frusto-conical in shape.

19. An inhaler as claimed in claim 1, wherein said cyclone chamber has a cylindrical section in the region of the air inlet.

20. An inhaler as claimed in claim 1, wherein the vortex finder is provided at approximately the same level as or below the air inlet.

21. An inhaler as claimed in claim 1, wherein the cyclone chamber comprises a base which generally conforms to part of a surface of a toroid.

22. An inhaler as claimed in claim 1, wherein the cyclone chamber comprises a base which is provided with a series of concentric ridges.

23. An inhaler as claimed in claim 1, wherein vertical ridges are provided in the cyclone chamber.

24. An inhaler as claimed in claim 1, wherein the surface of the wall of the cyclone chamber is treated to give an appropriate flow pattern.

25. An inhaler as claimed in claim 1, wherein the diameter of the cyclone chamber is between 5 and 100 mm.

26. An inhaler as claimed in claim 1, wherein the diameter of the cyclone chamber is between 5 and 50 mm.

27. An inhaler as claimed in claim 1, wherein the diameter of the cyclone chamber is between 8 and 20 mm.

28. A dry powder inhaler comprising:
a reverse flow cyclone chamber in which in use air and entrained substance particles circulate; said chamber comprising an axis and being elongate along said axis, an air inlet, a closed base and a vortex finder, said chamber being so shaped that at least a part of the chamber decreases in cross-sectional area in an axial direction away from the air inlet,
wherein the air inlet is arranged to direct air so that it circulates about the axis around the periphery of the chamber, and the vortex finder being arranged such that air exits therethrough after a reversal of axial direction at the base of the chamber to set up a reverse flow cyclone in the chamber in which air circulates in two generally concentric overlapping columns in opposite axial directions; and
wherein the vortex finder is arranged such that the entrained substance particles which are smaller than a predetermined size exit the chamber but the entrained substance particles which are larger than the predetermined size are retained in the chamber;
a mouthpiece in communication with said cyclone chamber;
wherein the cyclone chamber is provided by a part which is removable from the rest of the inhaler for regular replacement thereof.

29. An inhaler as claimed in claim 28, further comprising a bypass airflow path which bypasses the cyclone chamber.

30. A removable part for a dry powder inhaler, said part comprising a reverse flow cyclone chamber in which in use air and entrained substance particles circulate; said chamber comprising an axis and being elongate along said axis, an air inlet, a closed base and a vortex finder, said chamber being so shaped that at least a part of the chamber decreases in cross-sectional area in an axial direction away from the air inlet,
wherein the air inlet is arranged to direct air so that it circulates about the axis around the periphery of the chamber, and the vortex finder being arranged such that air exits therethrough after a reversal of axial direction at the base of the chamber to set up a reverse flow cyclone in the chamber in which air circulates in two generally concentric overlapping columns in opposite axial directions; and
wherein the vortex finder is arranged such that the entrained substance particles which are smaller than a predetermined size exit the chamber but the entrained substance particles which are larger than the predetermined size are retained in the chamber.

31. A portable, handheld, dry powder inhaler comprising:
a main airflow path including a reverse flow cyclone chamber in which in use air and entrained substance particles circulate, said chamber comprising an axis and being elongate along said axis, an inlet, a closed base and a vortex finder, said chamber being so shaped that at least a part of the chamber decreases in cross-sectional area in an axial direction away from the air inlet,
wherein the air inlet is arranged to direct air so that it circulates about the axis around the periphery of the chamber, and the vortex finder being arranged such that air exits therethrough after a reversal of axial direction at the base of the chamber to set up a reverse flow cyclone in the chamber in which air circulates in two generally concentric overlapping columns in opposite axial directions; and
wherein the vortex finder is arranged such that the entrained substance particles which are smaller than a predetermined size exit the chamber but the entrained substance particles which are larger than the predetermined size are retained in the chamber;
the inhaler further comprising a bypass airflow path bypassing the cyclone chamber;
wherein the main and bypass airflow paths communicate with a mouthpiece.

* * * * *

UNITED STATES PATENT AND TRADEMARK OFFICE
CERTIFICATE OF CORRECTION

PATENT NO. : 8,261,739 B2
APPLICATION NO. : 11/658693
DATED : September 11, 2012
INVENTOR(S) : David Stuart Harris and Simon James Smith It is certified that error appears in the above-identified patent and that said Letters Patent is hereby corrected as shown below:

In the Specifications:

Column 9
Line 35, "does" should read --dose--.

Column 11
Line 37, "5λm" should read --5μm--.

Column 12
Line 40, "41$a$" should read --41 $a$--.

Column 16
Line 3, "air" should read --air.--.

Signed and Sealed this
Fourteenth Day of May, 2013

Teresa Stanek Rea
*Acting Director of the United States Patent and Trademark Office*